United States Patent
Takenoshita et al.

(10) Patent No.: US 9,149,551 B2
(45) Date of Patent: Oct. 6, 2015

(54) PLASMA GENERATING DEVICE, PLASMA GENERATING METHOD, AND METHOD FOR SUPPRESSING OZONE GENERATION

(75) Inventors: Kazutoshi Takenoshita, Kanagawa (JP); Makoto Miyamoto, Kanagawa (JP); Seiro Yuge, Kanagawa (JP); Yuki Kumagai, Kanagawa (JP); Yoko Nakayama, Kanagawa (JP); Hideo Nojima, Kanagawa (JP); Myung Chul Kim, Suwon-Si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 77 days.

(21) Appl. No.: 13/884,469

(22) PCT Filed: Nov. 9, 2011

(86) PCT No.: PCT/JP2011/075819
§ 371 (c)(1),
(2), (4) Date: Sep. 19, 2013

(87) PCT Pub. No.: WO2012/063856
PCT Pub. Date: May 18, 2012

(65) Prior Publication Data
US 2014/0003994 A1    Jan. 2, 2014

(30) Foreign Application Priority Data
Nov. 9, 2010 (JP) .................... 2010-251168

(51) Int. Cl.
*A61L 2/00* (2006.01)
*A62B 7/08* (2006.01)
(Continued)

(52) U.S. Cl.
CPC . *A61L 9/015* (2013.01); *A61L 9/22* (2013.01); *H05H 1/2406* (2013.01); *A61L 2209/212* (2013.01); *H05H 2001/2412* (2013.01); *H05H 2245/121* (2013.01)

(58) Field of Classification Search
CPC ............. A61L 2/00; A61L 2/202; A61L 9/18; C01B 13/10
USPC ................. 422/22, 105, 121, 186.04, 186.07, 422/305–306, 906; 250/386, 324, 423 R; 204/164, 176
See application file for complete search history.

(56) References Cited

U.S. PATENT DOCUMENTS

2006/0042545 A1    3/2006   Shibata et al.

FOREIGN PATENT DOCUMENTS

| CN | 1331614 | 1/2002 |
| JP | 10-325560 | 12/1998 |

(Continued)

OTHER PUBLICATIONS
Japan Patent Office English Translation of the "Detailed Description" Section of JP 2009-078266.*
(Continued)

*Primary Examiner* — Monzer R Chorbaji
(74) *Attorney, Agent, or Firm* — Staas & Halsey LLP

(57) ABSTRACT

The purpose of the present invention is to minimize ozone production while increasing the production of an active species. The plasma generating device (100) comprises: a pair of electrodes (21, 22) in which dielectric films (21a, 21b) are disposed on at least one opposing face; voltage application means (4) for applying a pulse voltage across the electrodes (21, 22) to bring about a plasma discharger; and fluid circulation holes (21b, 22b) that are disposed in locations corresponding to the electrodes (21, 22), respectively, and that are configured to pass entirely therethrough. The plasma generating device is also configured such that a fluid passing through the fluid circulation holes (21b, 22b) comes into contact with the plasma, generating ions or radicals, wherein the voltage applying means (4) varies the peak value and/or the pulse width of the pulse voltage applied across the electrodes (21, 22).

18 Claims, 15 Drawing Sheets

(51) Int. Cl.
*B01J 19/08* (2006.01)
*H05F 3/00* (2006.01)
*A61L 9/015* (2006.01)
*A61L 9/22* (2006.01)
*H05H 1/24* (2006.01)

(56) References Cited

FOREIGN PATENT DOCUMENTS

| JP | 2006-302625 | | 11/2006 | |
| JP | 2009-078266 | * | 4/2009 | ............... B01J 19/08 |
| JP | 2009-78266 | | 4/2009 | |

OTHER PUBLICATIONS

International Search Report mailed Feb. 21, 2012 in corresponding International Application No. PCT/JP2011/075819.

Chinese Office Action issued Jul. 23, 2014 in corresponding Chinese Patent Application No. 201180064586.2.

Extended European Search Report mailed Jan. 12, 2015 in related European Application No. 11840063.9.

* cited by examiner

PLASMA GENERATING DEVICE, PLASMA GENERATING METHOD, AND METHOD FOR SUPPRESSING OZONE GENERATION

CROSS-REFERENCE TO RELATED APPLICATIONS

This application is a U.S. national stage application of PCT/JP2011/075819 filed Nov. 9, 2011 and claims foreign priority benefit of Japanese Application No. 2010-251168 filed Nov. 9, 2010 in the Japanese Intellectual Property Office, the contents of both of which are incorporated herein by reference.

TECHNICAL FIELD

The present invention relates to a plasma generator, a plasma generating method, and an ozone generation suppressing method to suppress generation of ozone in the plasma generator.

BACKGROUND ART

Recently, there is an increasing need for air quality control of a living environment such as sterilization and deodorization, due to increased risk of infection such as seen in an increase in carriers of atopy, asthma, and allergic symptoms and explosive prevalence of new influenza. In addition, as living becomes rich, an amount of food storage and a chance of storing leftover food are increased. Accordingly, the importance of environmental control in storage equipment represented as a refrigerator is also growing.

In the prior art for the purpose of controlling air quality of a living environment, physical control as represented by a filter is generally used. According to the physical control, relatively large dust and debris floating in the air may be captured, and bacteria, viruses, or the like may also be captured depending on the size of a filter hole. In addition, when there are an infinite number of adsorption sites such activated carbon, it may also be possible to capture malodorous molecules. However, there are problems in that air in a space to be controlled is required to evenly pass through the filter in order to be captured, the apparatus is increased in size, and a maintenance cost such as filter replacement is also increased while it has no effect on adhesive substances. Therefore, as a means to enable sterilization and deodorization of adhesive substances, it may be exemplified to release chemically active species to a space desired to perform sterilization and deodorization. In spraying of chemicals or release of flavoring agents or deodorant, it is necessary to prepare the active species in advance and regular replenishment thereof is essential. On the other hand, a means to perform sterilization and deodorization using the chemically active species generated by generating plasma in the atmosphere is increased in recent years.

Technologies to perform sterilization and deodorization by ions and radicals (hereinafter, referred to as "active species") generated by discharge of plasma into the atmosphere may be classified into the following two types:

(1) a so-called passive type plasma generator in which bacteria and viruses floating in the atmosphere (hereinafter, referred to as "floating bacteria") or malodorous substances (hereinafter, referred to as "odor") react with active species within a limited capacity in the apparatus (for example, Patent Document 1); and (2) a so-called active type plasma generator in which active species generated by a plasma generating portion are released into a closed space (e.g., a living room, a toilet, a car interior, or the like) having a larger capacity than (1) released into, and the active species in the atmosphere react with floating bacteria and odor by a collision therewith (for example, Patent Document 2).

The passive type plasma generator of (1) has an advantage that high sterilization and deodorization effects may be expected because active species of high concentration are generated by generation of plasma in the small capacity. On the other hand, the apparatus has a disadvantage that the size thereof is increased because floating bacteria and odor are required to be introduced into the apparatus, and a filter for adsorption or decomposition is required to be separately installed in order to prevent ozone from leaking out of the apparatus since the ozone is likely to occur as a by-product from plasma generation.

Next, the active type plasma generator of (2) has an advantage that the apparatus may be relatively small, and sterilization of bacteria adhered to a surface of clothing (hereinafter, referred to as "adhesive bacteria") and decomposition of odor adsorbed onto the surface may be expected in addition to sterilization of floating bacteria and decomposition of odor in the air. On the other hand, the apparatus has a disadvantage that only long-lived active species cannot help but expect sterilization and deodorization effects because active species are diffused within the closed space, which is very large compared to the volume of the apparatus, and have low concentration. As a result, the deodorization effect may not be nearly expected in a space having high odor concentration (high concentration 10,000 times the concentration of active species).

From the above, in the passive type plasma generator, the effect is limited only to floating bacteria and odor contained in an air stream flowing into the apparatus. On the other hand, in the active type plasma generator, the effect cannot help but be expected only with respect to floating bacteria, adhesive bacteria, and odor having low concentration. In other words, only either "sterilization and deodorization of floating bacteria" or "sterilization of floating bacteria and adhesive bacteria having low concentration and deodorization of adhesive odor" may be realized using the prior art.

However, there are some situations where sterilization of adhesive bacteria having high concentration and deodorization of odor having high concentration are required to be simultaneously performed in a daily life environment. The most typical example is a refrigerating chamber of a refrigerator in which many bacteria adhered to surfaces of food and a storage container surfaces exist and odor arising from food itself and decayed leftover food also exists.

CITATION LIST

Patent Document

Patent Document 1: Japanese Unexamined Patent Application Publication No. 2002-224211

Patent Document 2: Japanese Unexamined Patent Application Publication No. 2003-79714

DISCLOSURE

Technical Problem

Therefore, the present invention is a technique to simultaneously realize both sterilization and deodorization of adhesive bacteria, and it is a main object of the present invention to suppress a generation amount of ozone while increasing a generation amount of active species provide, so as to simultaneously include both a passive function which deodorizes adhesive bacteria using active species by generation of plasma and an active function which releases the active species outside an apparatus to sterilize the adhesive bacteria.

Technical Solution

In accordance with an aspect of the present invention, a plasma generator includes a pair of electrodes provided with a dielectric film on at least one facing surface thereof, a voltage applying unit which applies a pulse voltage between the electrodes to discharge plasma, and fluid circulation holes which are respectively provided at positions corresponding to the respective electrodes such that the respective electrodes are configured to be penetrated as a whole, the plasma generator is configured such that ions or radicals are generated by coming into contact with the plasma when fluid passes through the fluid circulation holes, wherein the voltage applying unit varies a peak value or a pulse width of the pulse voltage applied between the electrodes, or both thereof. Here, the corresponding positions mean that the fluid circulation holes formed in the pair of electrodes are substantially in the same positions and face each other when viewed from a face plate direction of each electrode. In addition, the corresponding positions mean the same substantially coordinate position (x, y) at both electrodes when viewing the pair of electrodes on the x-y plane from the z-axis direction in the orthogonal coordinate system.

In accordance with such a configuration, it may be possible to suppress a generation amount of ozone while increasing a generation amount of active species such as ions or radicals by applying the pulse voltage and varying the peak value or the pulse width of the pulse voltage, or both thereof.

As an aspect which realizes the peak value of the pulse voltage in order to suppress a generation amount of ozone while increasing a generation amount of active species such as ions or radicals, the voltage applying unit may adjust the peak value of the pulse voltage applied between the electrodes within a range of 500 V to 2000 V, preferably a range of 500 V to 2000 V, and more preferably a range of 800 V to 1400 V.

As an aspect which specifically realizes the pulse voltage, the half-width of the pulse voltage may be 300 μs or less. More preferably, the half-width of the pulse voltage may be 100 μs or less.

As an aspect which realizes the pulse width of the pulse voltage in order to suppress a generation amount of ozone while increasing a generation amount of active species such as ions or radicals, the voltage applying unit may adjust the pulse width of the pulse voltage applied between the electrodes within a range of 1 μs to 100 μs, and preferably a range of 1 μs to 50 μs.

When the peak value of the pulse voltage or the peak value is increased, the generation amount of ozone is increased. For this reason, in order to suitably reduce the generation amount of ozone, the voltage applying unit may perform an intermittent operation which repeats a voltage applying period which applies the pulse voltage between the electrodes in a predetermined period and an application stop period in which no pulse voltage is applied between the electrodes. In this case, in the intermittent operation, a ratio of the voltage applying period to one period of the intermittent operation may be 0.1 to 0.9, more preferably 0.3 to 0.8.

In order to meet the environmental standards configured to secure the plasma generator, ozone concentration, which is measured at a distance of 1 cm from the pair of electrodes, may be 0.1 ppm or less.

In order to increase the generation amount of active species while reducing power consumption, the voltage applying unit may apply a voltage such that a polarity of the pulse voltage is reversed after the peak thereof, and the reversed peak value is set to $1/100$ or more of an original peak value.

In accordance with another aspect of the present invention, a plasma generating method using a plasma generator including a pair of electrodes provided with a dielectric film on at least one facing surface thereof, a voltage applying unit which applies a pulse voltage between the electrodes to discharge plasma, and fluid circulation holes which are respectively provided at positions corresponding to the respective electrodes such that the respective electrodes are configured to be penetrated as a whole, the plasma generator being configured such that ions or radicals are generated by coming into contact with the plasma when fluid passes through the fluid circulation holes, the plasma generating method includes varying a peak value or a pulse width of the pulse voltage applied between the electrodes, or both thereof.

In accordance with a further aspect of the present invention, a method of suppressing ozone generation in a plasma plasma generator including a pair of electrodes provided with a dielectric film on at least one facing surface thereof, a voltage applying unit which applies a pulse voltage between the electrodes to discharge plasma, and fluid circulation holes which are respectively provided at positions corresponding to the respective electrodes such that the respective electrodes are configured to be penetrated as a whole, the plasma generator being configured such that ions or radicals are generated by coming into contact with the plasma when fluid passes through the fluid circulation holes, the method of suppressing ozone generation includes suppressing the ozone generation by varying a peak value or a pulse width of the pulse voltage applied between the electrodes, or both thereof.

Advantageous Effects

In accordance with the present invention having such a configuration, it may be possible to suppress a generation amount of ozone while increasing a generation amount of active species.

DESCRIPTION OF DRAWINGS

The above and other objects, features and other advantages of the present invention will be more clearly understood from the following detailed description taken in conjunction with the accompanying drawings, in which.

REFERENCE SIGNS LIST

Figure 1:
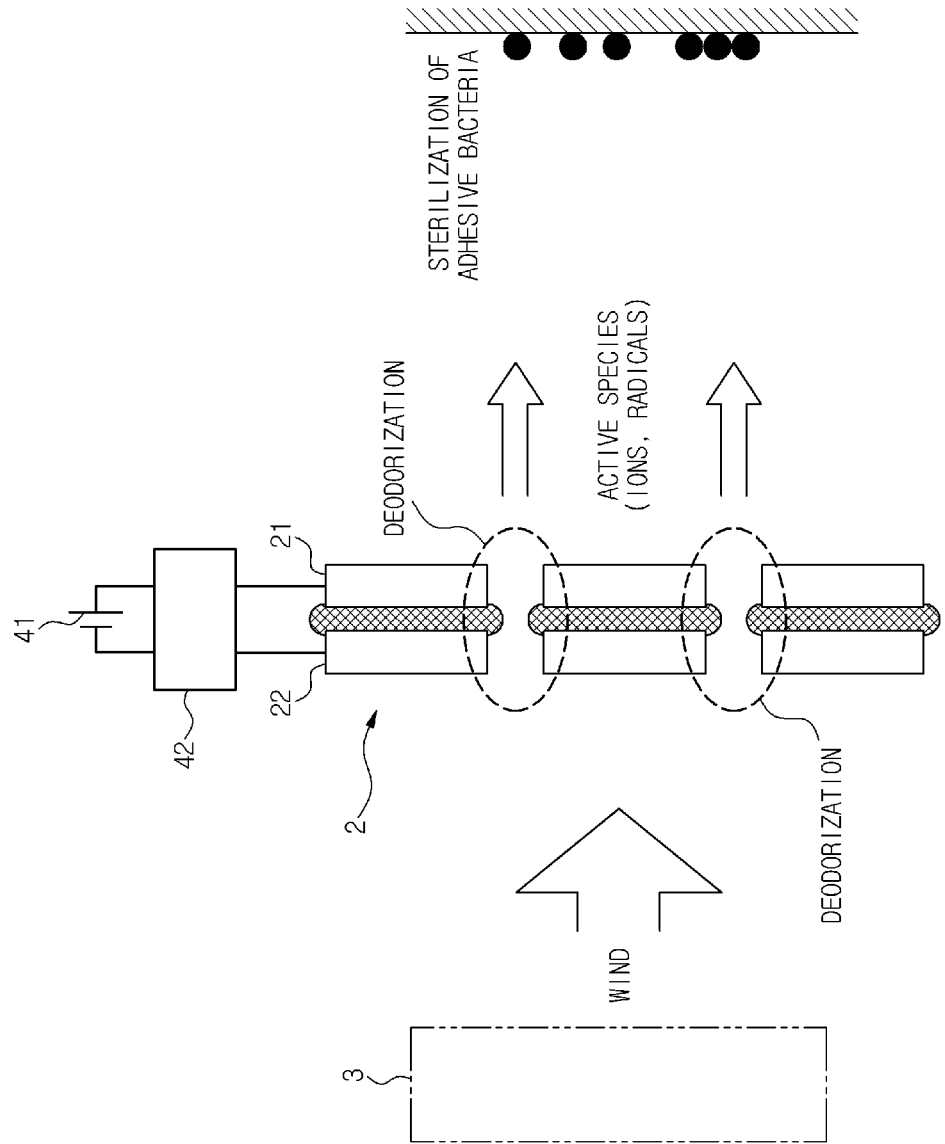
FIG. 1 is a view schematically illustrating a plasma generator according to an embodiment of the present invention.

100: a plasma generator
21: an electrode of one side
22: an electrode of the other side
21a, 22a: dielectric films
21b, 22b: fluid circulation holes
4: a voltage applying unit
41: a power source
42: a drive circuit portion

BEST MODE

Hereinafter, an embodiment of the present invention will be described with reference to the drawings.

A plasma generator 100 according to the present invention is used for a household appliance such as a refrigerator, a washing machine, a cleaner, a clothing dryer, an air conditioner, or an air cleaner, and serves to deodorize air in an indoor or outdoor of the household appliance and to sterilize floating bacteria or adhesive bacteria in the indoor or outdoor of the household appliance.

Specifically, as shown in FIG. 1, the plasma generator 100 includes a plasma electrode portion 2 to generate active species such as ions and radicals using Micro Gap Plasma, a blower mechanism 3 which is provided outside the plasma electrode portion 2 to forcibly blow wind (an air stream) toward the plasma electrode portion 2, and a voltage applying unit 4 which applies a predetermined voltage to the plasma electrode portion 2 to discharge plasma.

Hereinafter, the respective portions 2 to 4 will be described with reference to the drawings.

Figure 2:
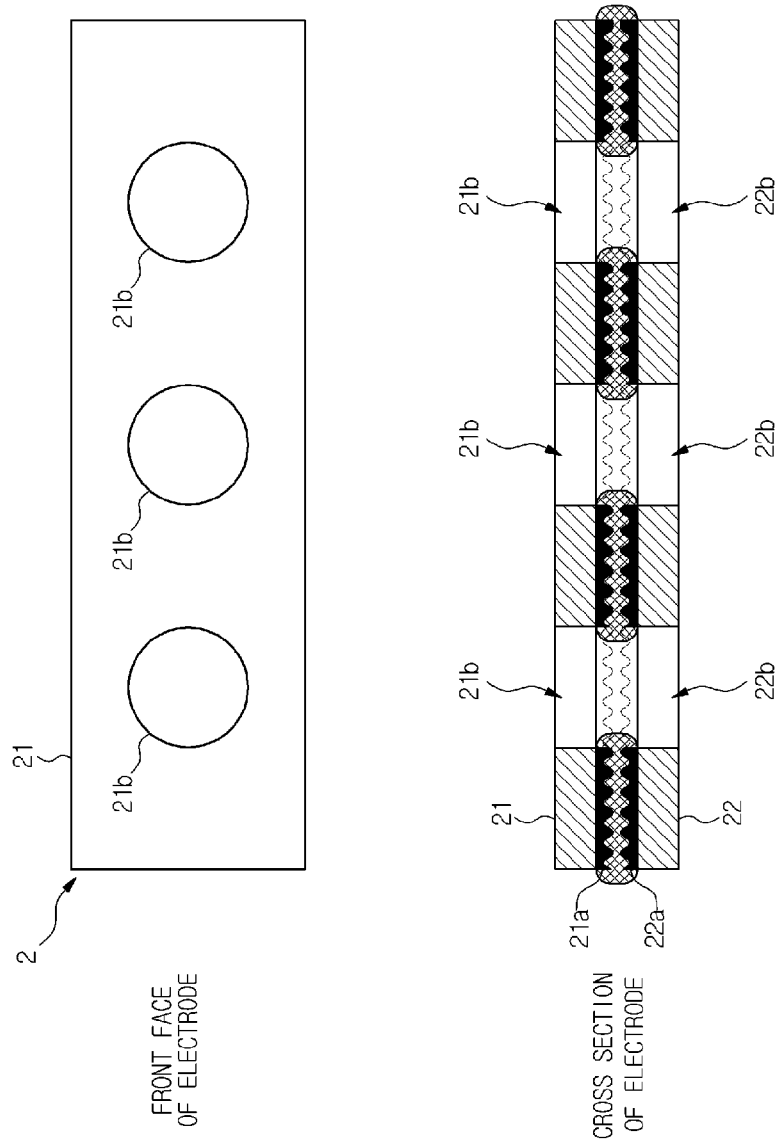
FIG. 2 is a partial enlarged top view and a cross-sectional view illustrating an electrode portion.

As shown in FIG. 2, the plasma electrode portion 2 has a pair of electrodes 21 and 22 provided with dielectric films 21a and 22a on respective facing surfaces thereof, and serves to apply a predetermined voltage between the electrodes 21 and 22 by the voltage applying unit 4 to discharge plasma. Each of the electrodes 21 and 22 has a substantially rectangular shape in the plan view (when viewed from a face plate direction of the electrode 21 or 22), and is made of stainless steel such as SUS403, for example. Although not shown, an edge portion of the electrode 21 or 22 of the electrode portion 2 is formed with an applied terminal to which a voltage is applied from the voltage applying unit 4.

In addition, as shown in FIG. 2, the respective facing surfaces of the electrodes 21 and 22 are formed with the dielectric films 21a and 22a by application of dielectric such as barium titanate, for example. The dielectric films 21a and 22a have surface roughness (calculation mean roughness Ra in the embodiment) of 0.1 μm to 100 μm. These other surface roughness may also be defined using a maximum height Ry and ten point mean roughness Rz. A gap is defined between the facing surfaces by adjusting plane roughness of the dielectric films 21a and 22a to a value within the above range and just overlapping the respective electrodes 21 and 22, so that plasma is generated within the gap. Thus, a spacer to define a gap for plasma formation between the respective electrodes 21 and 22 is not required. In addition, the surface roughness of the dielectric films 21a and 22a is considered to be controlled by sputtering. In addition, aluminum oxide, titanium oxide, magnesium oxide, strontium titanate, silicon oxide, silver phosphate, lead zirconate titanate, silicon carbide, indium oxide, cadmium oxide, bismuth oxide, zinc oxide, iron oxide, carbon nanotube, or the like may also be used as the dielectric applied to the electrodes.

Furthermore, the electrodes 21 and 22 are respectively provided with fluid circulation holes 21b and 22b at positions corresponding to the respective electrodes 21 and 22 such that the respective electrodes 21 and 22 are configured to be penetrated as a whole by communication of the fluid circulation holes 21b and 22b.

The blower mechanism 3 is disposed on the side of the other electrode 22 of the plasma electrode portion 2, and has a blowing fan which forcibly sends wind toward the fluid circulation holes (full opening portions) 21b and 22b formed in the plasma electrode portion 2. Specifically, the blower mechanism 3 allows a flow rate of the wind passing through the fluid circulation holes 21b and 22b to be within a range of 0.1 m/s to 10 m/s.

The voltage applying unit 4 includes a power source 41 and a drive circuit portion 42 which converts a voltage from the power source into a pulse voltage and applies the pulse voltage to each electrode. In addition, a specific configuration of the drive circuit portion 42 will be described later. The voltage applying unit 4 allows the voltage applied to each electrode 21 or 22 to be formed in a pulse shape, a peak value thereof to be within a range of 100V to 5000V, and a pulse width thereof to be within a range of 0.1 μs to 300 μs.

The plasma generator 100 having such a configuration performs deodorization in the vicinity of the electrodes 21 and 22 by generating plasma in the gap between two opposite electrodes 21 and 22 and sending wind to the fluid circulation holes 21b and 22b using the blower mechanism 3, and performs sterilization of adhesive bacteria by releasing active species generated in the plasma to a closed space. Here, since products generated in the plasma are wholly transported downstream by the wind, there is a need to limit generation of ozone harmful to a human body. Accordingly, by optimizing parameters of pulse voltage waveforms applied to the electrode 21 or 22 of the present embodiment, it may be possible to suppress ozone generation and enable both deodorization and sterilization.

Next, the following description will be given with respect to an experimental example using the plasma generator 100 of the present embodiment. The optimization of an electrode drive waveform is executed by air ion measurement and ozone concentration measurement in order to perform both sterilization and deodorization of adhesive bacteria. Both measurement are carried out in a distance which may install a measuring instrument downstream than the plasma electrode portion 2 (in this case, an inlet port is installed at the position of 1 cm in the ozone concentration measurement and at the position of 10 cm in the ion number density measurement). The air ion measurement is a method which is indirect, but is conveniently measured. In the air ion measurement method, although an object to be measured is ions which particularly have a charge and a long life among the active species generated in the plasma, a correlation between the air ion number density and the density of the active species is used under conditions of generating constant plasma. That is, the ion number density being high means that the density of the active species which are effective in sterilization and deodorization is high. Meanwhile, since ozone which is a by-product of plasma has a very long life (a few ten minutes or more) compared to ions, there is no significant difference between concentration in the vicinity of plasma and concentration at a point away from the downstream. Nevertheless, in order to increase the absolute value of a measured value and catch a small change in generation amount of ozone, a sampling inlet port of the measuring instrument is installed downstream apart from the electrode 21 by 1 cm. In such a measuring system, when the ion number density is maximized based on the ozone concentration, this is directly connected to the optimization of an electrode drive waveform shape.

Figure 3:
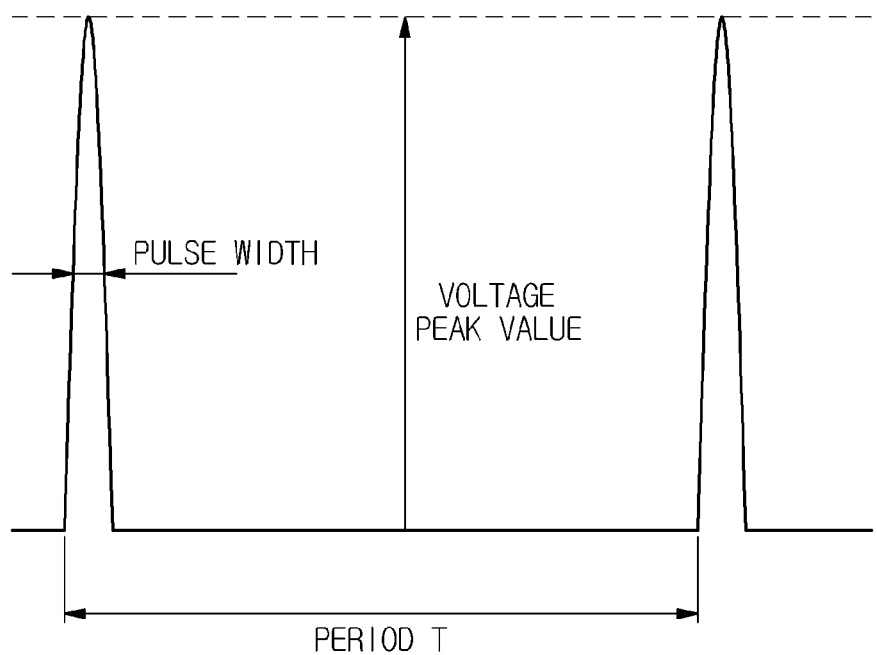
FIG. 3 is a diagram illustrating parameters of a pulse voltage waveform.

The drive circuit portion 42 is a pulse generation circuit to suppress ozone generation and increase generation of active species. A shown in FIG. 3, pulse shapes are defined as respective parameters. Since the gap distance between the electrodes 21 and 22 is equal to the surface roughness, in accordance with Paschen's law, a voltage peak value is in a range of 100 V to 5000 V, and a pulse width is defined by the half-width and is within a range of 0.1 μs to 300 μs.

Figure 4:
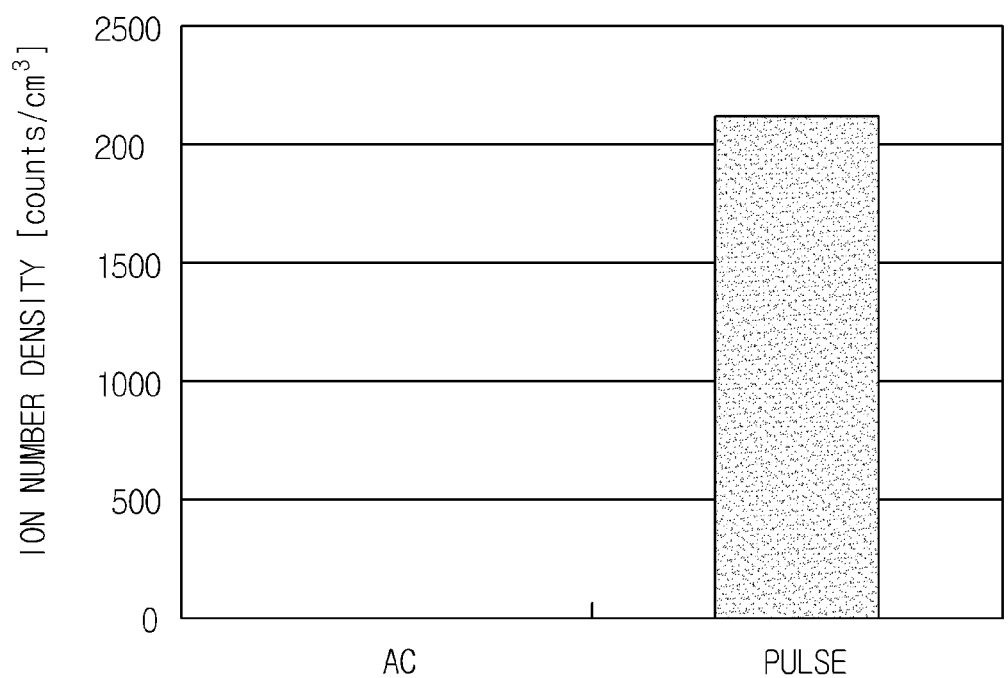
FIG. 4 is a graph illustrating a difference in ion number density according to a drive method.
Figure 5:
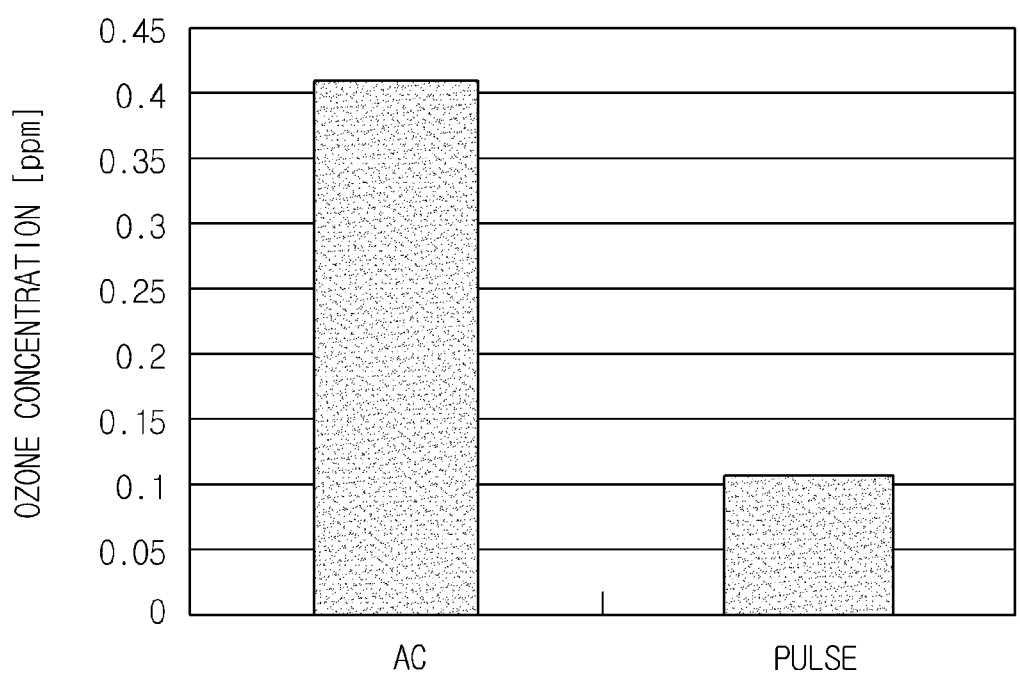
FIG. 5 is a graph illustrating a difference in ozone concentration according to a drive method.

Although it is possible to generate plasma by applying a high voltage to the electrodes 21 and 22, FIGS. 4 and 5 show a comparison between when an AC voltage is applied and when a pulse voltage of the present embodiment is applied. The AC voltage allows a peak voltage to be adjusted to 1000 V and frequency to be adjusted to 60 Hz using an external transformer and a variable autotransformer. On the other hand, the pulse voltage allows a peak value of a voltage having the pulse width of 5 μs to be adjusted to 1000 V and pulse repetition frequency to be adjusted to 60 Hz so that they are adjusted to be equal to those of the AC voltage and are applied. As shown in FIG. 4, when the AC voltage is applied, the generation of ions may not be confirmed. As shown in FIG. 5, on the other hand, ozone is measured at very high concentration. On the other hand, when the pulse voltage is applied, a generation amount which is sufficient to measure the ion number is confirmed, and the concentration of ozone is also measured at concentration lower than when the AC voltage is applied. Therefore, it is understood that the pulse voltage drive is effective to suppress the ozone generation and increase the generation amount of ions, namely, active species.

Figure 6:
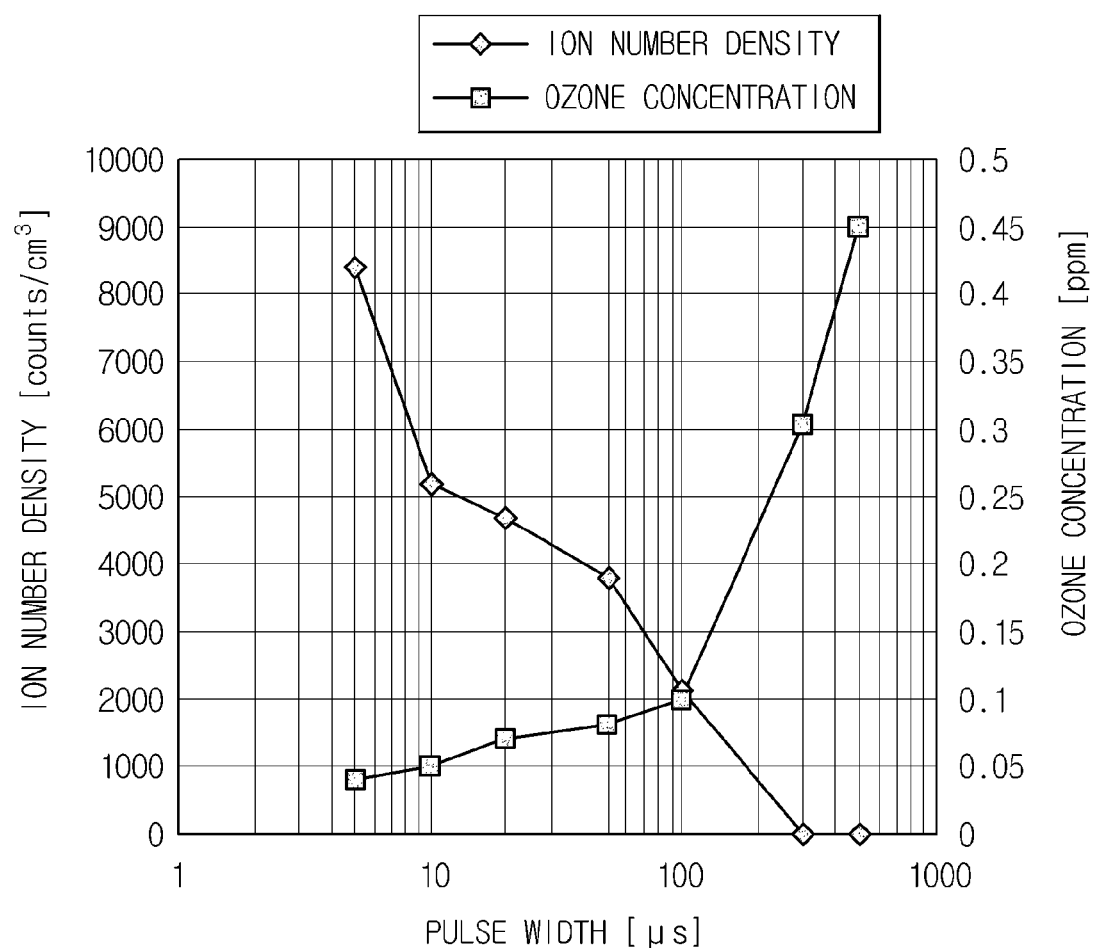
FIG. 6 is a graph illustrating pulse width dependence of the ion number density and the ozone concentration.

Furthermore, the generation amount of active species may be increased by controlling the pulse width of the high voltage pulse to be small. Pulse width dependence of ion number density and ozone concentration shown in FIG. 6 is measurement when the pulse repetition frequency and the peak voltage value are constantly kept as 1 k and only the pulse width is varied. As shown in FIG. 6, the ion number is measured and the ozone concentration is decreased in a pulse width of 100 μs or less. Therefore, as the pulse width becomes small, the ion number is increased and the ozone concentration is decreased.

Figure 7:
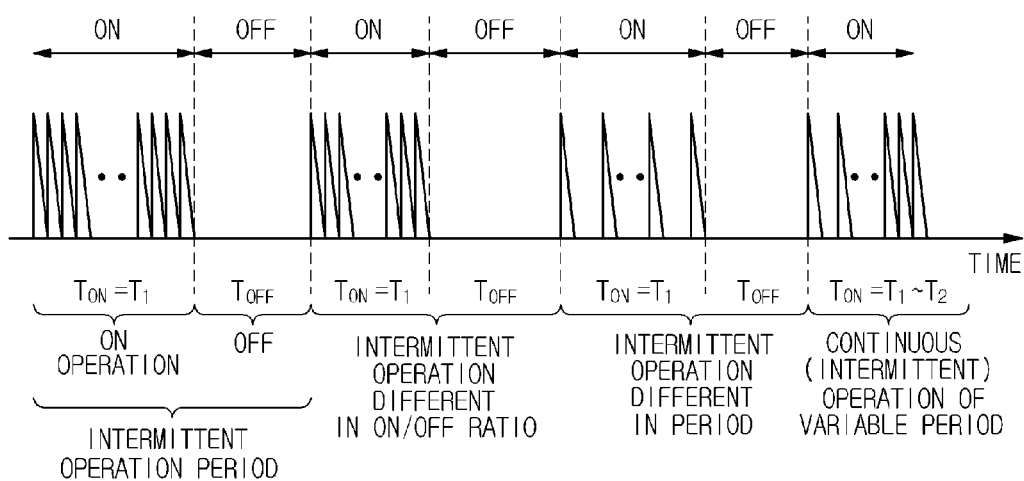
FIG. 7 is a diagram illustrating a representative example of an intermittent operation.

In addition to the means to suppress the generation amount of ozone and increase the generation amount of ions by reducing the pulse width as described above, the generation amount of active species per unit time may be increased by means of a method of controlling repetition of the pulse voltage using the drive circuit portion 42. When repetition frequency of a certain constant pulse voltage is increased, the generation amount of ozone per unit time is increased. Therefore, as shown in FIG. 7, it may be possible to suppress the generation amount of ozone and increase only the ion number density by performing an intermittent operation which repeats a voltage applying period ("ON operation ($T_{ON}$)" in FIG. 7) which applies the pulse voltage between the pair of electrodes in a predetermined period and an application stop period ("OFF ($T_{OFF}$)" in FIG. 7) in which no pulse voltage is applied to the pair of electrodes. In other words, it may be possible to control the generation of more dense active species by controlling a time ratio of the ON operation ($T_{ON}$) and the OFF operation ($T_{OFF}$) (a duty ratio ($=T_{ON}/(T_{ON}+T_{OFF})$)), or by uniformizing or varying the pulse repetition period in the ON operation.

Figure 8:
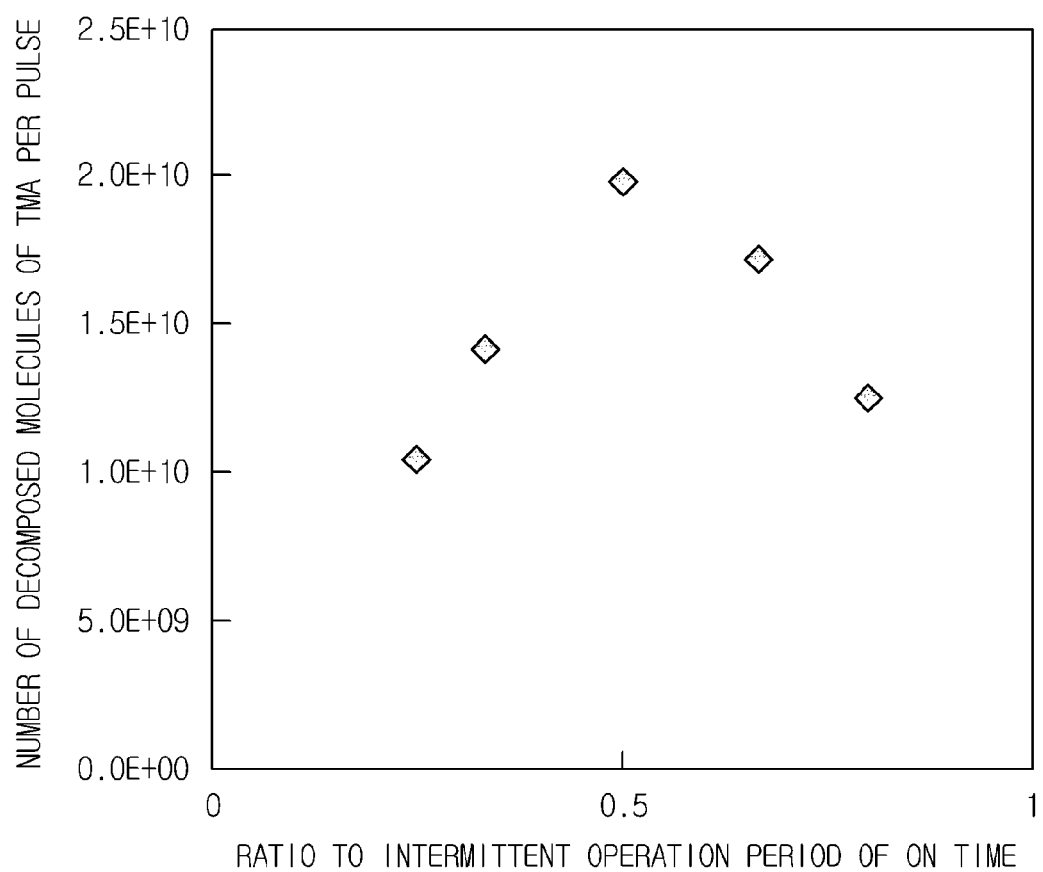
FIG. 8 is a graph illustrating a difference depending on an ON/OFF ratio of an intermittent operation of deodorization ability.

FIG. 8 shows a change in deodorization ability when ON time of the intermittent operation is changed in a case of uniformizing the peak voltage of the and the pulse width of the pulse voltage, as an example of increasing the generation amount of active species by the intermittent operation. The deodorization ability is obtained from the decomposition rate of odor when, at room temperature, 2 ppm of trimethylamine (TMA) as odor is injected into a 100 L capacity container made of resin and the ion generator 100 of the present embodiment is intermittently operated. As shown in FIG. 8, the deodorization ability is determined as being changed depending on a ratio to the intermittent operation period of ON time. This indicates that the optimum conditions exist by a balance between the concentration of generated active species and the concentration of decomposed odor, so that the optimization of the deodorization ability may be realized by the optimization of the drive method.

Figure 9:
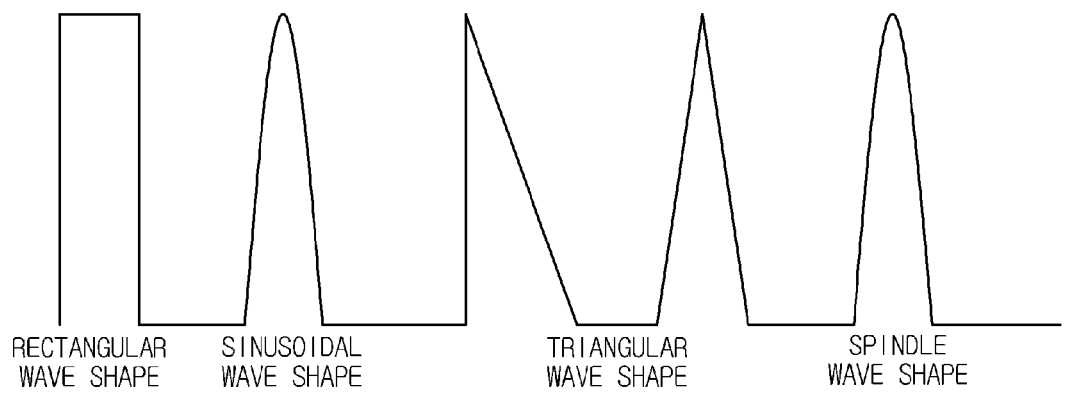
FIG. 9 is a diagram illustrating types of pulse width waveforms.

As shown in FIG. 9, an example of a representative pulse shape includes a rectangular wave shape, a sinusoidal wave shape, a triangular wave shape, or a spindle wave shape. The waveform other than the rectangular wave is a waveform in which a width is decreased as a voltage is increased. In addition, the pulse shape also includes a waveform in which the voltage rises along a saturation curve associated with the charging and discharging of a load and the voltage drops along an attenuation curve. Furthermore, in the detailed shape of the pulse wave, the pulse wave includes a symmetrical waveform in which a shape during the voltage rise and a shape during the voltage drop are equal to each other, and an asymmetrical waveform in which the respective shapes differ from each other. Actually, the generation of plasma results in the same effects that after the voltage becomes sufficiently high, the duration of the discharge is less than the half-width, and the pulse width becomes smaller.

Figure 10:
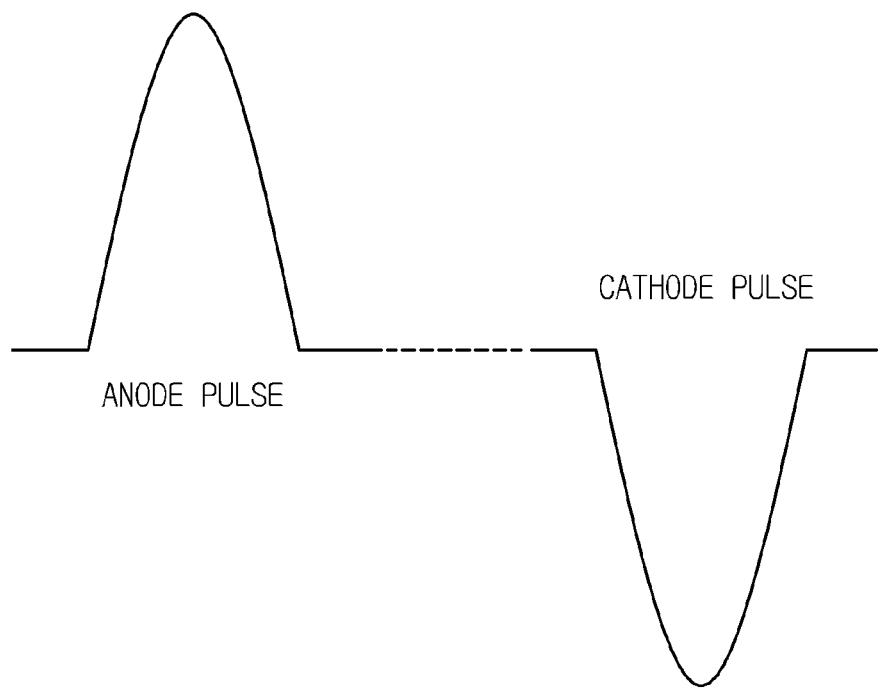
FIG. 10 is a diagram schematically illustrating a polarity of a pulse voltage.

As shown in FIG. 10, in the polarity of the pulse voltage, the pulse is an anode pulse in which a positive voltage is applied to the electrode 22 of the other side when the electrode 21 of one side is grounded, a cathode pulse in which a negative voltage is applied to the electrode 22, or both thereof.

Figure 11:
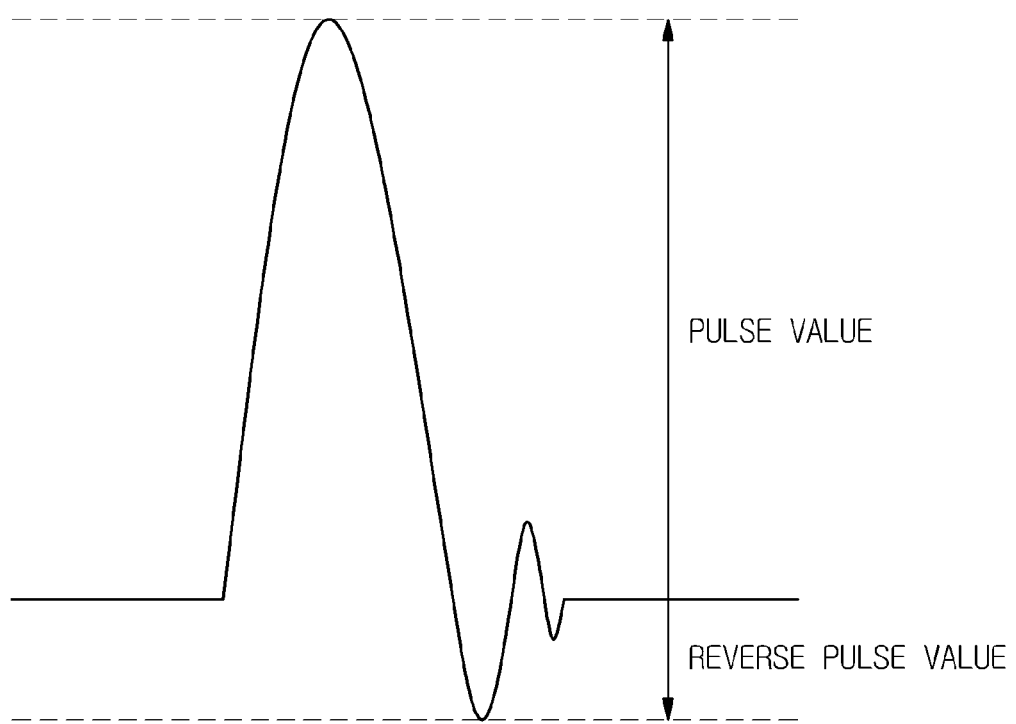
FIG. 11 is a diagram schematically illustrating a reverse pulse.

In addition, when the cathode pulse is applied, as shown in FIG. 11, power consumption may be reduced by a reverse pulse such as overshoot after the peak. In this case, the same effect as the applied cathode pulse may be expected by the reverse pulse of 1/100 or more of an anode pulse value. In other words, equivalent active species may be generated at approximately half of the power applied to both anode and cathode pulses.

Figure 12:
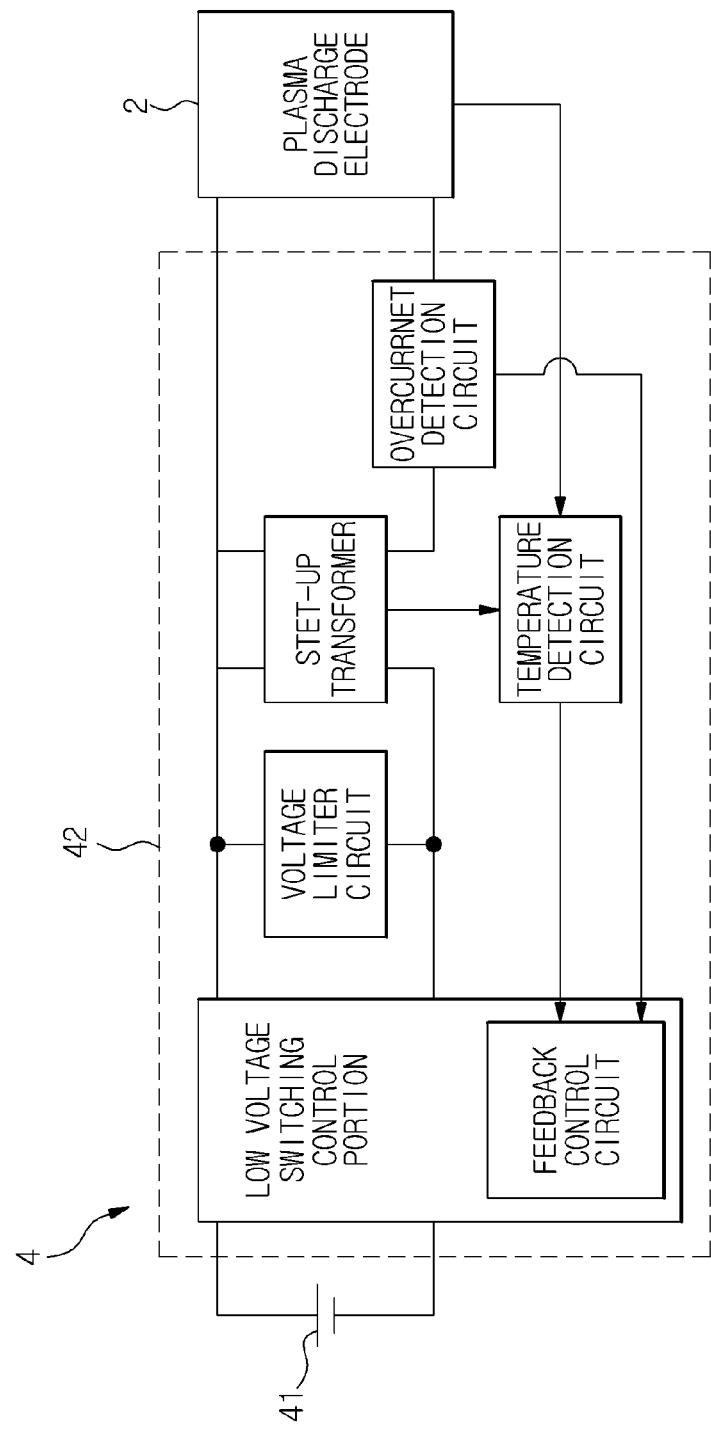
FIG. 12 is a block diagram illustrating a drive circuit portion.

In order to achieve such a pulse drive circuit portion 42, a switching element and a step-up transformer are combined from a DC voltage, so that it may be possible to suppress the power consumption and simplify the circuit. As an example of the drive circuit portion 42, as shown in FIG. 12, a low voltage pulse by the switching control from a DC low voltage is given to a first side of the step-up transformer, thereby generating a high voltage pulse corresponding to a winding ratio of the transformer at a second side thereof. The high voltage pulse is applied to the connected plasma discharge electrodes, and thus plasma is generated between the electrodes and active species which are effective in sterilization and deodorization are generated.

The peak voltage of the high voltage pulse may be controlled by increasing and decreasing switching time using a low voltage switching control portion. The control portion is used together with an element having temperature characteristic, thereby serving as a feedback circuit to sense a change in temperature by heating of the transformer and a change in environmental temperature of the electrode portion. In addition, the control portion may compensate a change in generation amount of active species caused by the change in temperature change by adjusting the switching time.

In addition, a maximum peak value of the high voltage pulse is limited by a voltage limiter circuit which is connected in parallel to the first side of the step-up transformer, a high voltage more than needs is applied to wiring between second side windings of the transformer or up to the electrodes, and to the electrodes themselves, so that safety may be enhanced without the occurrence of phenomena such as a short circuit. On the other hand, when a reduction in short circuit is generated, this is detected by an overcurrent detection circuit (for example, sensing the voltage of a micro-resistance end) which is connected in series with respect to the electrodes on the second side of the transformer, and is fed back to the feedback control circuit incorporated in the low voltage switching control portion. Therefore, latch control is performed so as not to generate a short-circuit phenomenon caused by the generation of an overcurrent again, and a region to which the second side high voltage of the transformer is applied is protected.

Figure 13:
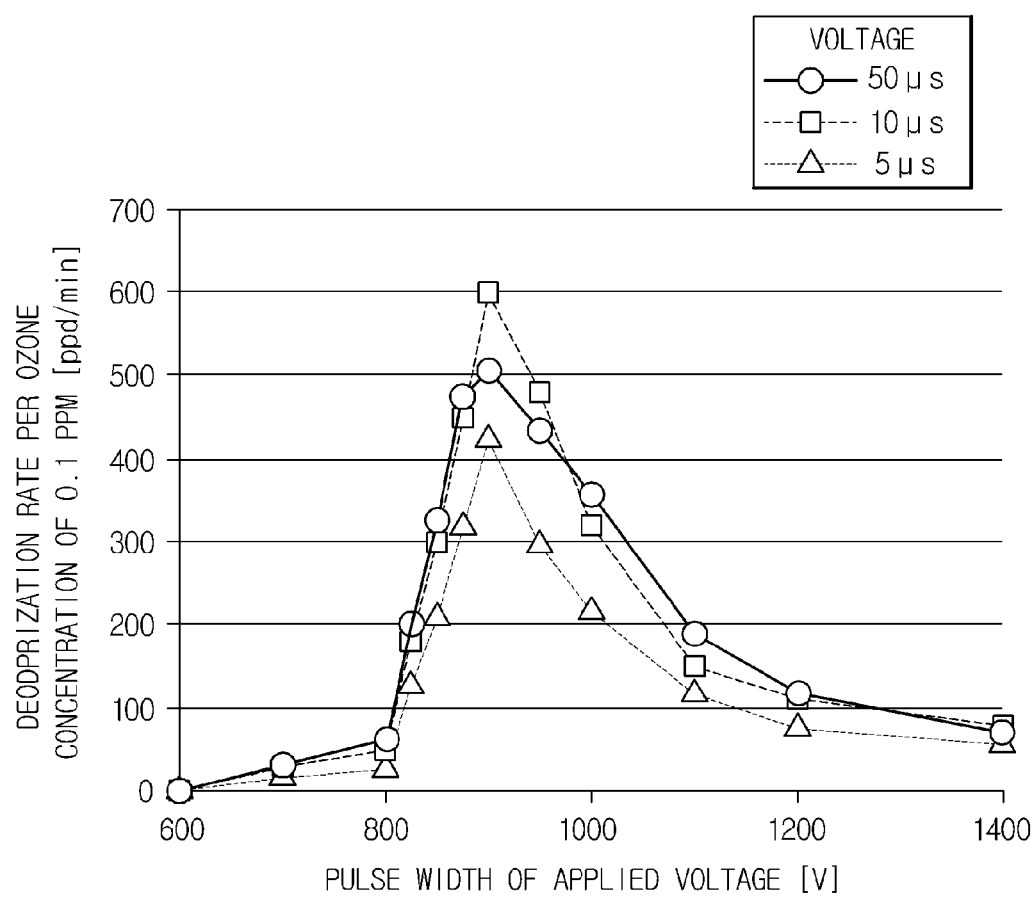
FIG. 13 is a graph illustrating peak voltage dependence of an applied voltage of a deodorization rate around 0.1 ppm concentration of ozone.
Figure 14:
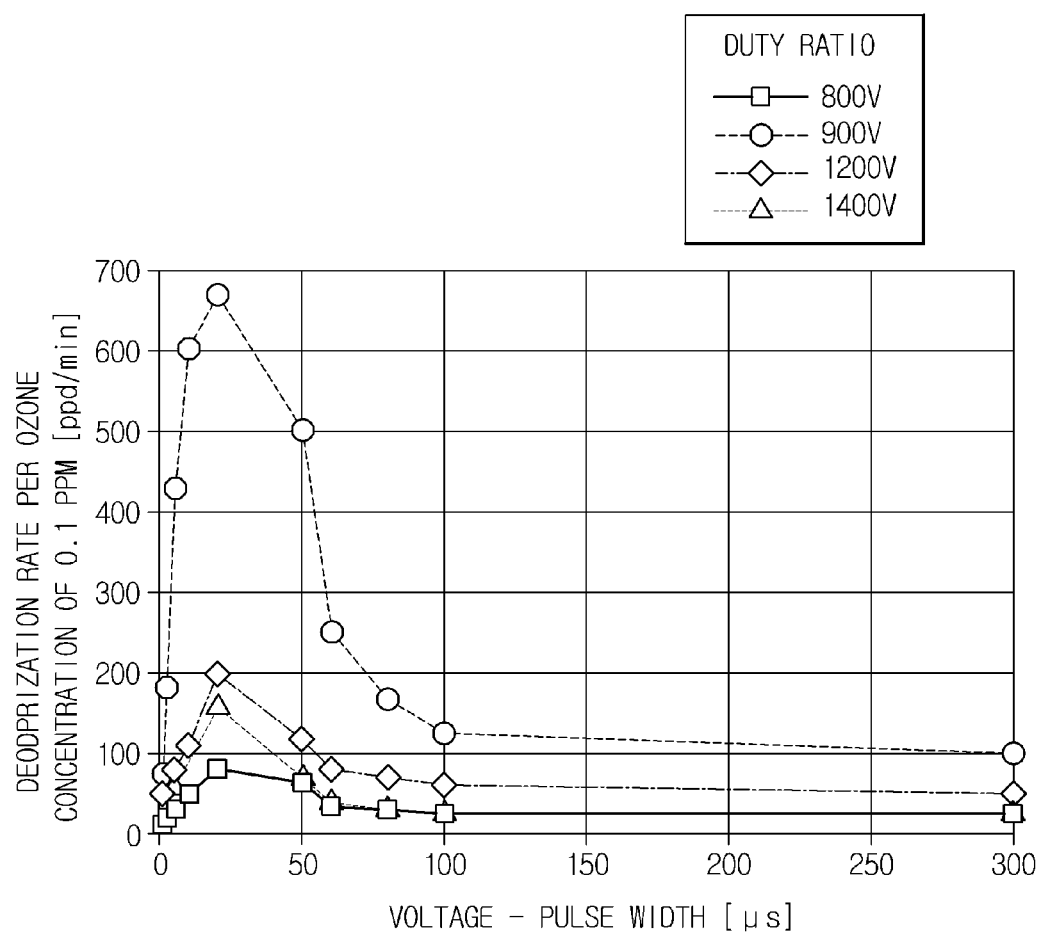
FIG. 14 is a graph illustrating pulse width dependence of an applied voltage of a deodorization rate around 0.1 ppm concentration of ozone.
Figure 15:
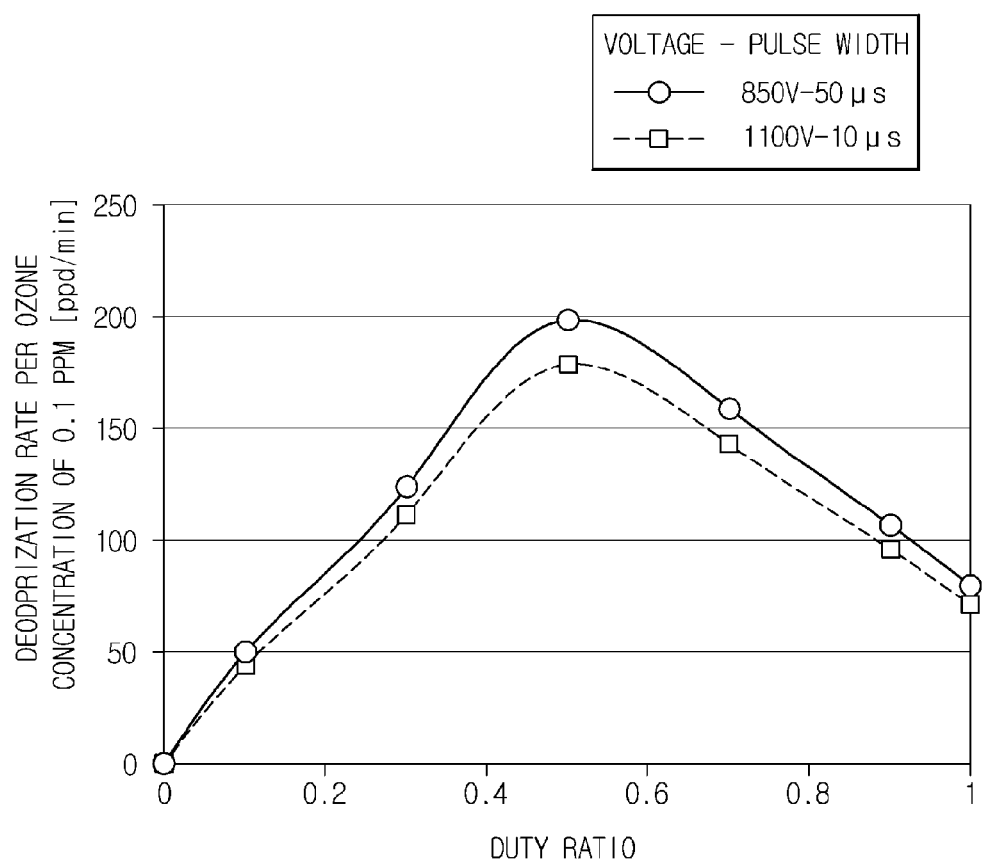
FIG. 15 is a graph illustrating duty ratio dependence of an intermittent operation of a deodorization rate around 0.1 ppm concentration of ozone.

Next, FIGS. 13 to 15 show deodorization performance when each parameter of an applied voltage is varied by the voltage applying unit. In a deodorization performance experiment, a deodorization rate is obtained from the concentration of a residual odor component after, at room temperature, the plasma generator of the present embodiment is installed within a 100 L capacity container made of resin, methyl mercaptan as the odor component is injected into the container, and the plasma generator is operated for 2 hours. In the following, ozone concentration generated from the plasma generator is made so that the ozone concentration measured at a distance of 1 cm from the pair of electrodes is set to 0.1 ppm or less.

FIG. 13 shows a deodorization rate (ppb/min) when the ozone concentration is set to 0.1 ppm and the peak voltage is varied from 600 V to 1400 V in the plasma generator. In addition, FIG. 13 shows results of a case where the pulse width is fixed to 50 μs and the peak value is varied from 600 V to 1400 V, a case where the pulse width is fixed to 10 μs and the peak value is varied from 600 V to 1400 V, and a case where the pulse width is fixed to 5 μs and the peak value is varied from 600 V to 1400 V.

As can be seen from FIG. 13, even in a case where the pulse width is in any of 50 μs, 10 μs, and 5 μs, it may be seen that the deodorization rate is increased when the peak value of the applied voltage is varied from 600 V to 900 V, and the deodorization rate is decreased, after set to the maximum deodorization rate of 900 V, when the peak value of the applied voltage is varied from 900 V to 1400 V. As a result, even in any pulse width, the peak value of the pulse voltage is preferably set from 800 V to 1400 V.

Next, FIG. 14 shows a deodorization rate (ppb/min) when the ozone concentration is set to 0.1 ppm and the pulse width of the pulse voltage is varied from 0 μs to 300 μs in the plasma generator. In addition, FIG. 14 shows results of a case where the peak value is fixed to 800 V and the pulse width is varied from 0 us to 300 μs, a case where the peak value is fixed to 900 V and the pulse width is varied from 0 μs to 300 μs, a case where the peak value is fixed to 1200 V and the pulse width is varied from 0 μs to 300 μs, and a case where the peak value is fixed to 1400 V and the pulse width is varied from 0 μs to 300 μs.

As can be seen from FIG. 14, even in a case where the peak value is in any of 800 V, 900 V, 1200 V, and 1400 V, it may be seen that the deodorization rate is fast until the pulse width is approximately 50 μs, and the deodorization rate is decreased due to ozone generation when the pulse width is increased more than the 50 μs.

Next, FIG. 15 shows a deodorization rate (ppb/min) when the ozone concentration is set to 0.1 ppm and the ratio (duty ratio in FIG. 15) of the voltage applying period to one period of the intermittent operation of the pulse voltage is varied from 0 to 1. In addition, as shown in FIG. 7, the intermittent operation is an operation repeating the voltage applying period ($T_{ON}$) which applies the pulse voltage between the electrodes in a predetermined period and the application stop period ($T_{OFF}$) in which no pulse voltage is applied between the electrodes, and the duty ratio is defined as $T_{ON}/(T_{ON}+T_{OFF})$. FIG. 15 shows results of a case where the peak voltage is set to 850 V and the pulse width intermittently operates the pulse voltage of 50 μs, and a case where the peak voltage is set to 1100 V and the pulse width intermittently operates the pulse voltage of 10 μs.

As can be seen from FIG. 15, the deodorization rate is fast as the duty ratio is increased, but the deodorization rate is decreased when the duty ration exceeds 0.5 of approximately half. Since the generation amount of ozone is increased when the duty ratio is larger, but the reaction with odor with respect the same is not increased, there exists a maximum value in duty ratio dependence of the deodorization rate.

In accordance with the plasma generator 100 according to the present embodiment having such a configuration, since the pulse voltage is applied and the pulse voltage is set so that the half-width is 300 μs or less, it may be possible to suppress the generation amount of ozone while increasing the generation amount of active species such as ions or radicals.

In addition, the present invention is not limited to the above embodiment, and various modifications are possible without departing from the scope and spirit of the invention.

INDUSTRIAL APPLICABILITY

In accordance with the present invention, it may be possible to suppress a generation amount of ozone while increasing a generation amount of active species.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A plasma generator including a pair of electrodes provided with a dielectric film on at least one facing surface thereof, a voltage applying unit which applies a pulse voltage between the electrodes to discharge plasma, and fluid circulation holes which are respectively provided at positions corresponding to the respective electrodes such that the respective electrodes are configured to be penetrated as a whole, the plasma generator being configured such that ions or radicals are generated by coming into contact with the plasma when fluid passes through the fluid circulation holes, wherein the voltage applying unit varies a peak value or a pulse width of the pulse voltage applied between the electrodes, or both thereof,
wherein the voltage applying unit is configured to adjust the pulse width of the pulse voltage applied between the electrodes within a range of 1 μs to 100 μs.

2. The plasma generator according to claim 1, wherein the width of the applied pulse voltage is a full width at half maximum.

3. The plasma generator according to claim 1, wherein the voltage applying unit adjusts the pulse width of the pulse voltage applied between the electrodes within a range of 1 μs to 50 μs.

4. The plasma generator according to claim 1, wherein the voltage applying unit adjusts the peak value of the pulse voltage applied between the electrodes within a range of 100 V to 5000 V.

5. The plasma generator according to claim 1, wherein the voltage applying unit adjusts the peak value of the pulse voltage applied between the electrodes within a range of 500 V to 2000 V.

6. The plasma generator according to claim 1, wherein the voltage applying unit adjusts the peak value of the pulse voltage applied between the electrodes within a range of 800 V to 1400 V.

7. The plasma generator according to claim 1, wherein the voltage applying unit performs an intermittent operation which repeats a voltage applying period which applies the pulse voltage between the electrodes in a predetermined period and an application stop period in which no pulse voltage is applied between the electrodes.

8. The plasma generator according to claim 7, wherein in the intermittent operation, a ratio of the voltage applying period to one period of the intermittent operation is 0.1 to 0.9.

9. The plasma generator according to claim 7, wherein in the intermittent operation, a ratio of the voltage applying period to one period of the intermittent operation is 0.3 to 0.8.

10. The plasma generator according to claim 1, further comprising a blower mechanism to forcibly blow wind toward the fluid circulation holes.

11. The plasma generator according to claim 1, wherein ozone concentration, which is measured at a distance of 1 cm from the pair of electrodes, is 0.1 ppm or less.

12. The plasma generator according to claim 1, wherein surface roughness of the dielectric film is 0.1 μm to 100 μm.

13. The plasma generator according to claim 1, wherein the voltage applying unit applies a voltage such that a polarity of the pulse voltage is reversed after the peak thereof, and the reversed peak value is set to $1/100$ or more of an original peak value.

14. The plasma generator according to claim 1, wherein the pulse voltage has a pulse shape which is a rectangular wave shape, a sinusoidal wave shape, a triangular wave shape, or a spindle wave shape.

15. The plasma generator according to claim 1, wherein the pulse shape of the pulse voltage also includes a waveform in which a voltage rises along a saturation curve associated with charging and discharging of a load and a voltage drops along an attenuation curve.

16. The plasma generator according to claim 1, wherein the pulse shape of the pulse voltage includes a symmetrical waveform in which a shape when a voltage rises and a shape when a voltage drops are equal to each other, and an asymmetrical waveform in which the respective shapes differ from each other.

17. A plasma generating method using a plasma generator including a pair of electrodes provided with a dielectric film on at least one facing surface thereof, a voltage applying unit which applies a pulse voltage between the electrodes to discharge plasma, and fluid circulation holes which are respectively provided at positions corresponding to the respective electrodes such that the respective electrodes are configured to be penetrated as a whole, the plasma generator being configured such that ions or radicals are generated by coming into contact with the plasma when fluid passes through the fluid circulation holes, the plasma generating method comprising:
varying a peak value or a pulse width of the pulse voltage applied between the electrodes, or both thereof,
wherein the pulse width of the pulse voltage applied between the electrodes is adjusted within a range of 1 μs to 100 μs.

18. A method of suppressing ozone generation in a plasma generator including a pair of electrodes provided with a dielectric film on at least one facing surface thereof, a voltage applying unit which applies a pulse voltage between the electrodes to discharge plasma, and fluid circulation holes which are respectively provided at positions corresponding to the respective electrodes such that the respective electrodes are configured to be penetrated as a whole, the plasma generator being configured such that ions or radicals are generated by coming into contact with the plasma when fluid passes through the fluid circulation holes, the method of suppressing ozone generation comprising:
suppressing the ozone generation by varying a peak value or a pulse width of the pulse voltage applied between the electrodes, or both thereof,
wherein the pulse width of the pulse voltage applied between the electrodes is adjusted within a range of 1 μs to 100 μs.

* * * * *